United States Patent [19]
Kondo et al.

[11] Patent Number: 4,983,605
[45] Date of Patent: * Jan. 8, 1991

[54] PHARMACEUTICAL COMPOSITION

[75] Inventors: Nobuo Kondo, Daito; Masahiro Kikuchi, Mino; Tsunetaka Nakajima, Kashiwara; Masahiro Watanabe, Akashi; Kazumasa Yokoyama, Toyonaka; Takahiro Haga, Kusatsu; Nobutoshi Yamada; Hideo Sugi, both of Moriyama; Toru Koyanagi, Kyoto, all of Japan

[73] Assignees: Ishihara Sangyo Kaisha Ltd.; The Green Cross Corporation, both of Osaka, Japan

[ * ] Notice: The portion of the term of this patent subsequent to Jul. 18, 2006 has been disclaimed.

[21] Appl. No.: 110,284

[22] Filed: Oct. 20, 1987

Related U.S. Application Data

[63] Continuation-in-part of Ser. No. 824,088, Jan. 30, 1986, Pat. No. 4,849,425.

[30] Foreign Application Priority Data

Oct. 23, 1986 [JP] Japan .................. 61-253079
Jun. 30, 1987 [JP] Japan .................. 62-164497

[51] Int. Cl.$^5$ .............. A01N 43/58; A01N 43/54; A01N 47/28
[52] U.S. Cl. .................. 514/247; 514/274; 514/327; 514/594; 514/595; 514/597; 514/598; 514/961; 514/964; 514/346
[58] Field of Search .............. 514/594, 596, 597, 598, 514/960, 961, 964, 346, 247, 274, 327

[56] References Cited

U.S. PATENT DOCUMENTS

| | | | |
|---|---|---|---|
| 3,535,423 | 10/1970 | Ordas .................. | 514/596 |
| 3,920,442 | 11/1975 | Albert et al. .......... | 514/596 |
| 3,992,553 | 11/1976 | Sirrenberg et al. ..... | 514/594 |
| 4,083,977 | 4/1978 | Miesel ................. | 514/249 |
| 4,085,226 | 4/1978 | Sirrenberg et al. ..... | 514/596 |
| 4,366,155 | 12/1982 | Canada ................. | 514/247 |
| 4,727,077 | 2/1988 | Haga et al. ........... | 514/274 |
| 4,849,421 | 7/1989 | Kondo et al. .......... | 514/946 |
| 4,904,668 | 2/1990 | Kondo et al. .......... | 514/274 |

FOREIGN PATENT DOCUMENTS

| | | |
|---|---|---|
| 77759 | 4/1983 | European Pat. Off. . |
| 192263 | 3/1986 | European Pat. Off. . |
| 178572 | 4/1986 | European Pat. Off. . |
| 233559 | 8/1987 | European Pat. Off. . |
| 8302230 | 7/1983 | Int'l Pat. Institute . |
| 57-109721 | 7/1982 | Japan . |
| 8318620 | 5/1984 | Netherlands .......... 564/44 |

OTHER PUBLICATIONS

Chemical Abstracts, vol. 73, No. 20, Nov. 16, 1979, p. 226, Abstract No. 102065z, Columbus, OH, U.S.A. & CS-A-133 277 (L. Burda et al.) 08-15-1969.

Primary Examiner—H. M. S. Sneed
Assistant Examiner—J. Saba
Attorney, Agent, or Firm—Oblon, Spivak, McClelland, Maier & Neustadt

[57] ABSTRACT

A pharmaceutical composition comprising a benzoyl urea compound (A) selected from the group consisting of a benzoyl urea compound (I) having the formula:

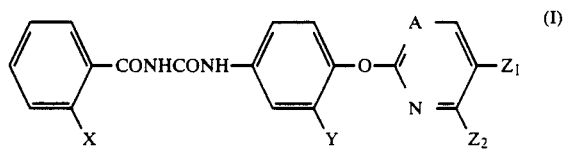

wherein X is a halogen atom, a nitro group or a trifluoromethyl group, provided that when Y is a nitro group, X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom, and A is a =CH— group or a nitrogen atom, and a benzoyl urea compound (II) having the formula:

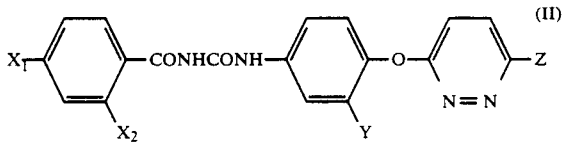

wherein each of $X_1$ and $X_2$ is a hydrogen atom, a halogen atom or a nitro group, provided that when Y is a nitro group, $X_1$ is a hydrogen atom, Y is a hydrogen atom, a halogen atom, a nitro group or a trifluoromethyl group, and Z is a hydrogen atom, a halogen atom or a trifluoromethyl group, as an active ingredient; a nonionic surfactant as a dispersant; and at least one member selected from the group consisting of a saccharide, a saccharide alcohol, silicic anhydride and a nonionic surfactant, as a disintegrator.

10 Claims, No Drawings

PHARMACEUTICAL COMPOSITION

This is a continuation-in-part of application Ser. No. 06/824,088 filed Jan. 30, 1986, now U.S. Pat. No. 4,849,425 granted Jul. 18, 1989.

The present invention relates to an antitumour pharmaceutical composition containing a benzoyl urea compound as an active ingredient. More particularly, the present invention relates to a pharmaceutical composition containing an antitumour benzoyl urea compound (A) selected from the group consisting of a benzoyl urea compound (I) having the formula:

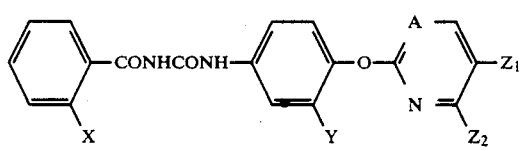

wherein X is a halogen atom, a nitro group or a trifluoromethyl group, provided that when Y is a nitro group, X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom, and A is a =CH— group or a nitrogen atom, and a benzoyl urea compound (II) having the formula:

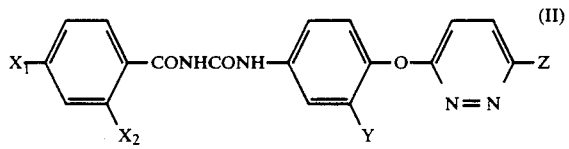

wherein each of $X_1$ and $X_2$ is a hydrogen atom, a halogen atom or a nitro group, provided that when Y is a nitro group, $X_1$ is a hydrogen atom, Y is a hydrogen atom, a halogen atom, a nitro group or a trifluoromethyl group, and Z is a hydrogen atom, a halogen atom or a trifluoromethyl group and having improved the absorbability of the compound (A) through the gut. (The benzoyl urea compounds (I) and (II) will generally be referred to as a benzoyl urea compound (A) hereinafter.)

The benzoyl urea compound (A) is substantially a known compound, and it is known to have excellent antitumour activities (Japanese Unexamined Patent Publications Nos. 109721/1982, 1670/1986, 33176/1986, No. 93163/1986, No. 5959/1987 and No. 116566/1987). However, this compound is hardly soluble in water, and its absorbablity through e.g. the gut is poor. Therefore, in order to obtain adequate antitumour activities, it is necessary to increase the dose, whereby there is a possible danger of adverse effects due to the excessive administration.

It is an object of the present invention to provide a pharmaceutical composition whereby a benzoyl urea compound (A) has an improved absorbability through the gut.

The present inventors have conducted extensive research, on various additives with an aim to improve the absorbability of the benzoyl urea compound (A) through the gut, and as a result, have found it possible to increase the absorbability of the benzoyl urea compound (A) through the gut by a composition (particularly by a dry formulation) prepared by using specific substances i.e. specific dispersant and disintegrator. The present invention has been accomplished based on this discovery.

The present invention provides a pharmaceutical composition comprising a benzoyl urea compound (A) selected from the group consisting of the above-identified benzoyl urea compounds (I) and (II), as an active ingredient; a nonionic surfactant as a dispersant; and at least one member selected from the group consisting of a saccharide, a saccharide alcohol, silicic anhydride and a nonionic surfactant, as a disintegrator.

Now, the present invention will be described in detail with reference to the preferred embodiments.

The benzoyl urea compound (A) used as the active ingredient of the present invention includes a benzoyl urea compound (I) having the formula:

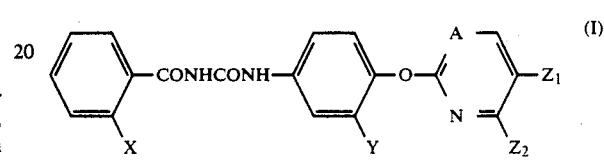

wherein X is a halogen atom, a nitro group or a trifluoromethyl group, provided that when Y is a nitro group, X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom, and A is a =CH— group or a nitrogen atom, and a benzoyl urea compound (II) having the formula:

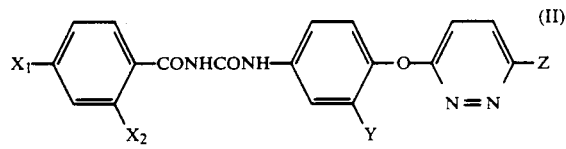

wherein each of $X_1$ and $X_2$ is a hydrogen atom, a halogen atom or a nitro group, provided that when Y is a nitro group, $X_1$ is a hydrogen atom, Y is a hydrogen atom, a halogen atom, a nitro group or a trifluoromethyl group, and Z is a hydrogen atom, a halogen atom or a trifluoromethyl group.

The following compounds may be mentioned as typical examples of the benzoyl urea compound (A) to be used in the present invention.

(Compound No. 1)

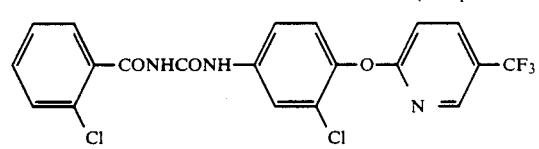

(Compound No. 2)

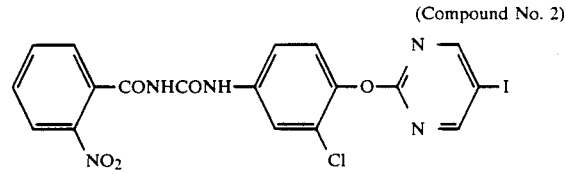

-continued

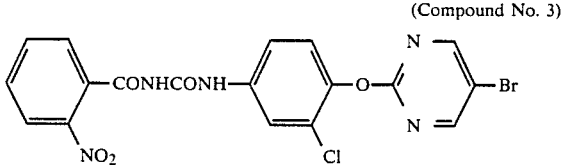
(Compound No. 3)

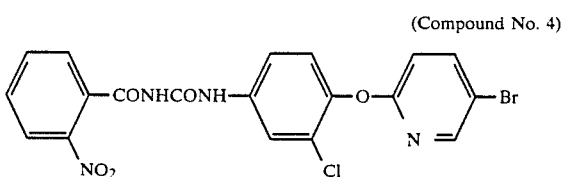
(Compound No. 4)

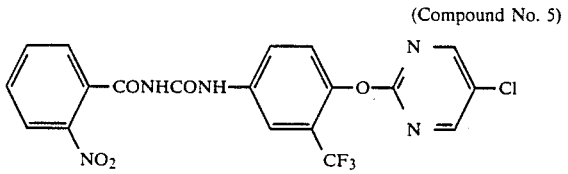
(Compound No. 5)

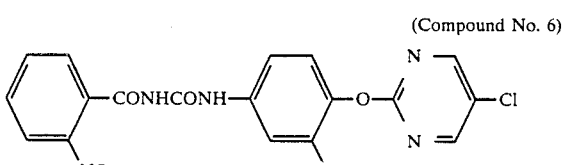
(Compound No. 6)

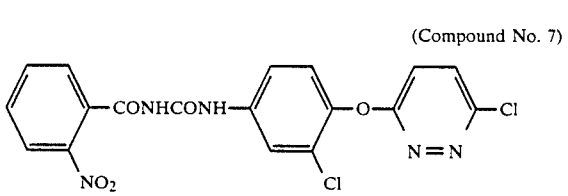
(Compound No. 7)

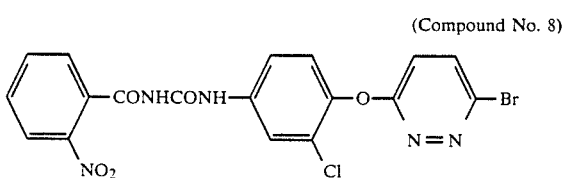
(Compound No. 8)

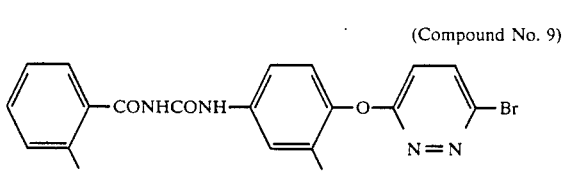
(Compound No. 9)

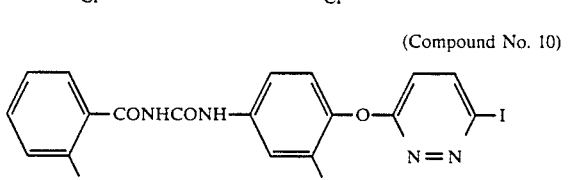
(Compound No. 10)

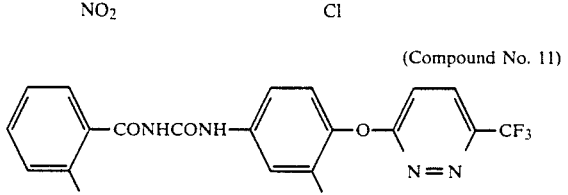
(Compound No. 11)

The benzoyl urea compound (A) is substantially a known compound, and it may be prepared by a method disclosed in e.g. Japanese Unexamined Patent Publication Nos. 109721/1982, 1670/1986, 33176/1986, 93163/1986, 227572/1986, 5959/1987, 116566/1987 or 135463/1987 or by a similar method.

In the preparation of the pharmaceutical composition of the present invention, it is desirable to pulverize the benzoyl urea compound (A) as fine as possible. The dispersant used in the present invention serves as dispersant when the benzoyl urea compound (A) is formed into an aqueous solution for the purpose of pulverization. There is no particular restriction as to the nonionic surfactant to be used as the dispersant, so long as it is useful for the purpose of the present invention. Any nonionic surfactant may be employed, which is useful as an additive for pharmaceuticals. Its HLB value (Hydrophile-Lipophile Balance) is preferably at least 3. Specific examples of such nonionic surfactants include polyoxyethylene hardened castor oil, polyoxyethylene polyoxypropylene glycol, a sucrose fatty acid ester, a glycerol fatty acid ester, a sorbitan fatty acid ester, a propylene glycol fatty acid ester, a polyglycerol fatty acid ester, a polyoxyethylene sorbitan fatty acid ester, a polyoxyethylene sorbitol fatty acid ester, a polyoxyethylene glycerol fatty acid ester, a polyethylene glycol fatty acid ester and a polyoxyethylene castor oil.

Among the above-mentioned nonionic surfactants, preferred are a polyoxyethylene hardened ester oil, a polyoxyethylene polyoxypropylene glycol and a polyglycerol fatty acid ester.

The disintegrator used in the present invention is added at the time of freeze-drying the benzoyl urea compound (A) to improve the granularity and disintegrating property of the formulation. As such a disintegrator, a saccharide, a saccharide alcohol, silicic anhydride or a nonionic surfactant may be employed.

The saccharide as the disintegrator includes a monosaccharide such as glucose or fructose, a disaccharide such as sucrose, maltose or lactose and a polysaccharide such as starch, dextrin or cellulose.

The saccharide alcohol as the disintegrator includes, for example, mannitol and sorbitol.

As the silicic anhydride as the disintegrator, light silicic anhydride may be employed.

The nonionic surfactant as the disintegrator includes polyoxyethylene hardened castor oil, polyoxyethylene polyoxypropylene glycol, a sucrose fatty acid ester, a glycerol fatty acid ester, a sorbitan fatty acid ester, a propylene glycol fatty acid ester, a polyglycerol fatty acid ester, a polyoxyethylene sorbitan fatty acid ester, a polyoxyethylene sorbitol fatty acid ester, a polyoxyethylene glycerol fatty acid ester, a polyethylene glycol fatty acid ester and a polyoxyethylene castor oil.

As the disintegrator, a nonionic surfactant is preferably used. Particularly preferred is a sucrose fatty acid ester or a polyoxyethylene polyoxypropylene glycol.

The nonionic surfactant as the dispersant and the nonionic surfactant as the disintegrator may be the same, but preferably they are different from each other. For instance, it is preferred to use a sucrose fatty acid ester as the disintegrator when a polyglycerol fatty acid ester (e.g. decaglycerol monolaurate) or a polyoxyethylene hardened castor oil (e.g. polyoxyethylene hardened castor oil 60) is used as the dispersant.

The pharmaceutical composition of the present invention is prepared preferably by pulverizing the benzoyl urea compound (A) in an aqueous solution containing a dispersant, then adding the disintegrator thereto, followed by freeze-drying.

The pulverization is preferably conducted by wet pulverization. The wet pulverization is a method wherein the material to be pulverized is rotated or shaked together with beads (particularly glass beads) in a solution containing the dispersant. A machine such as Dyno-mill (KDL-model, manufactured by Willy A. Bachofen Company) may be employed for this purpose. The concentration of the benzoyl urea compound in the aqueous solution during the pulverization, is from 1 to 70 w/v %, preferably from 20 to 50 w/v %. Particularly when the pulverization is conducted in a wet pulverization system by using Dyno-mill, the concentration of the benzoyl urea compound in the aqueous solution is preferably within the above range. The concentration of the nonionic surfactant as a dispersant is usually from 1 to 30 w/v %, preferably from 2 to 20 w/v %. The glass beads employed usually have a size of from 0.1 to 1.5 mm in diameter, preferably from 0.25 to 0.5 mm in diameter. The pulverization time is usually from 5 minutes to 1 hour.

The composition prepared by the wet pulverization under the above-mentioned condition, has the average particle size of from 0.2 to 1.0 μm (light-scattering method).

After the completion of the wet pulverization, glass beads will be removed by sieving. Then, the disintegrator is added to the solution of the pulverized benzoyl urea compound (A), followed by freeze-drying. The concentration of the disintegrator is from 1 to 90 w/v %, preferably from 10 to 70 w/v %.

The pharmaceutical composition, particularly the dry formulation, of the present invention has a ratio of the benzoyl urea compound (A) : dispersant : disintegrator of, for example, 1 to 70:1 to 30:1 to 90 by weight, preferably 20 to 50:2 to 20:10 to 70 by weight The pharmaceutical composition, particularly the dry formulation, of the present invention can be formulated into pharmaceutical formulations by conventional methods. As such pharmaceutical formulations, oral formulations such as powders, fine particles, granules, capsules, tablets and liquid drugs may be mentioned.

The pharmaceutical composition, particularly the dry formulation, of the present invention may usually be administered orally to mammals (e.g. human beings, horses, cattles, dogs, mice, rats, etc.). The dose varies depending upon the diseased condition, the sex, the body weight, the formulation, etc. However, for instance, when the composition of the present invention is orally administered against human malignant lymphoma or lung cancer, it is administered in a daily dose of from 5 to 100 mg/kg as the benzoyl urea compound (A) to an adult in one to three times per week.

The pharmaceutical composition, particularly the dry formulation, of the present invention has excellent granularity, disintegrating property and stability. Further, the absorption of the benzoyl urea compound (A) through the gut is thereby remarkably improved.

By using the pharmaceutical composition, particularly the dry formulation, of the present invention, it is possible to reduce the dose of the benzoyl urea compound (A) and thus to reduce the side effects or the pain to the the patient when it is administered to the patient.

TEST EXAMPLE 1

Type of the Disintegrator

The difference in the granularity and disintegrating property depending upon the type of the disintegrator was studied.

The dry formulation product was prepared in the same manner as in the after-mentioned Example 1 except for using 10 w/v % of Compound 3, 8.8 w/v % of HCO-60 (manufactured by Nikko Chemical K.K.) and 30 w/v % of a disintegrator. The disintegrating property and granularity were examined, and the results are shown in Table 1.

Further, the dry formulation was prepared in the same manner as in Example 1 except for using 20 w/v % of a disintegrator. The disintegrating property and granularity were examined, and the results are shown in Table 2.

The disintegrating property was evaluated as follows: 10 ml of a 1% HCO-60 aqueous solution and glass beads having a diameter of 7 mm were added to the dry formulation thus prepared (containing 10 mg of the benzoyl urea compound (A)), and the mixture was rotated at 30 rpm for 1 hour. The disintegrating property is represented by the proportion (%) of the benzoyl urea compound (A) passed through a membrane filter having a pore size of 0.8 μm.

TABLE 1

| Disintegrator | | Disintegrating property (%) | Granularity |
| --- | --- | --- | --- |
| Saccharide | Lactose | 57.7 | agglomerate |
| | Starch | 51.4 | " |
| | Dextrin | 48.5 | " |
| | Celullose | 8.8 | powder |
| Saccharide alcohol | Mannitol | 57.9 | agglomerate |
| | Sorbitol | 50.4 | " |
| Silicic anhydride | Light silicic anhydride | 20.9 | powder |

TABLE 2

| Disintegrator | | | Disintegrating property (%) | Granularity |
| --- | --- | --- | --- | --- |
| | General Name | Tradename | | |
| Nonionic surfactant | Polyoxyethylene hardened castor oil | HCO-100 (Nikko Chemical K.K.) | 29.8 | agglomerate |
| | Polyoxyethylene polyoxypropylene glycol | PLURONIC F68 (Asahi Denka kogyo K.K.) | 15.9 | powder |
| | Sucrose fatty acid ester | P1670 (Mitsubishi Chemical Industries Ltd.) | 13.7 | " |
| | Polyoxyethylene fatty acid ester | MYS 40 (Nikko Chemical K.K.) | 16.5 | agglomerate |
| | Not added | | 2.0 | powder |

TEST EXAMPLE 2

Concentration of the Disintegrator

The granularity and disintegrating property of the formulation of the present invention depending upon the concentration of the disintegrator were examined, and the results are shown in Table 3. The examination was conducted in the same manner as in Example 1 except for varying the concentration of the disintegrator.

TABLE 3

| Disintegrator | Content (w/v %) | Disintegrating property (%) | Granularity |
|---|---|---|---|
| PLURONIC F68 | 10 | 11.5 | powder |
|  | 20 | 24.0 | " |
|  | 30 | 36.6 | " |
|  | 40 | 36.4 | " |
| P1670 | 10 | 15.1 | powder |
|  | 20 | 32.4 | " |
|  | 40 | 53.4 | " |

TEST EXAMPLE 3

Stability

The formulation obtained in Example 1 was stored at 60° C. for 4 weeks, whereupon it was confirmed that 97% of Compound No. 3 remained.

TEST EXAMPLE 4

Pharmaceutical Effect

The pharmaceutical effect of the dry formulation of the present invention was examined.

$10^5$ of mouse lymphoid leukemia cell L-1210 per mouse were intraperitoneally transplanted to $BDF_1$ mouse (male, from 20 to 22 g). Each formulation was orally administered 1 and 8 days after the transplantation. Each formulation was formed into a liquie suspension, and administered to each mouse in an amount of 0.5 ml per mouse. Then, the mortality was observed. The results are shown in Table 4.

The activity was evaluated by a survival rate [T/C (%)] as compared with a control group to which a physiological saline was administered.

$$T/C\ (\%) = \frac{\text{Median survival time of test animals}}{\text{Median survival time of control animals}} \times 100$$

TABLE 4

| Administered formulation | Dose | T/C (%) |
|---|---|---|
| The formulation of | 400 | 208 |
| the present invention | 200 | 195 |
| (The formulation of) | 100 | 177 |
| (Example 1) | 50 | 116 |
| The aqueous suspension | 400 | 117 |
| of Compound No. 3 | 200 | 109 |
| Physiological saline (control) |  | 100 |

TEST EXAMPLE 5

Concentration in Blood

The formulation of the present invention was forcibly orally administered by an oral sonde to a group of two Wister male rats (body weight: 50 g) starved for 18 hours (dose as Compound No. 3: 200 mg/5 ml/kg). Then, blood (0.3 ml) was periodically sampled with heparin from the jugular vein.

The blood thus obtained was subjected to separation of the plasma and removal of proteins by using acetonitrile, and then Compound No. 3 was quantitatively analyzed by a high speed liquid chromatography using a reversed phase column (Nova Pak $C_{18}$, 5μ, 3.9 mm in diameter ×150 mm, Nihon Waters), and the curve of the concentration in blood was prepared.

From the curve of the concentration in blood, the area below the curve was obtained by using a trapezoid formula and presented as AUC (Area Under the Curve). The respective values were obtained for all rats, and the average value and the width are shown in Table 5.

TABLE 5

| Administered formulation | AUC (μg/ml · hr) |
|---|---|
| The formulations of the present invention |  |
| The formulation of |  |
| Example 1 | 11.25 ± 3.68 |
| Example 2 | 13.86 ± 4.51 |
| Example 3 | 13.62 ± 2.95 |
| The aqueous suspension of Compound No. 3 | 2.41 ± 0.88 |

EXAMPLE 1

Compound No. 3 (20 g) was suspended in 50 ml of a 5 w/v % HCO-60 aqueous solution, and the suspension was wet pulverized (3000 rpm for 45 minutes) by Dyno-mill by using 50 g of glass beads (from 0.25 to 0.5 mm in diameter). After the completion of the pulverization, glass beads were removed by sieving, to obtain a wet pulverized formulation of Compound No. 3.

To 50 ml of the liquid formulation thus obtained, 20 g of a sucrose fatty acid ester (P1670, manufactured by Mitsubishi Chemical Industries Ltd.) was added. The mixture was freezed with dry ice-methanol and then subjected to vacuum drying for 24 hours to remove water. The freeze-dried formulation thus obtained was filled in capsules to obtain capsule drugs.

EXAMPLE 2

Compound No. 3 (15 g) was suspended in 50 ml of a 5 w/v % polyoxyethylene w/v% polyoxyethylene polyoxypropylene glycol (PLURONIC F 68) aqueous solution, and the suspension was wer pulverized (3000 rpm for 45 minutes) by Dyno-mill by using 50 g of glass beads (from 0.25 to 0.5 mm in diameter). After the completion of the pulverization, glass beads were removed by sieving, to obtain a wet pulverized formulation of Compound No. 3.

To 50 ml of the liquid formulation thus obtained, 30 g of a sucrose fatty acid ester (P1670, manufactured by Mitsubishi Chemical Industries, Ltd ) was added. The mixture was freezed with dry ice-methanol and then subjected to vacuum drying for 24 hours to remove water. The freeze-dried formulation thus obtained was filled in capsules to obtain capsule drugs.

EXAMPLE 3

A good dry formulation was obtained in the same manner as in Example 2 except for using decaglycerol monolaurate (Decagline IL manufactured by Nikko Chemical K.K.) in place of the polyoxyethylene polyoxypropylene glycol.

We claim:

1. A pharmaceutical composition consisting essentially of an antitumor benzoyl urea compound (A) selected from the group consisting of a benzoyl urea compound (I) having the formula:

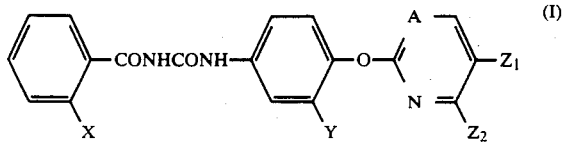

wherein X is a halogen atom, a nitro group or a trifluoromethyl group, provided that when Y is a nitro group, X is a halogen atom or a nitro group, Y is a hydrogen atom, a halogen atom, a nitro group or a trifluoromethyl group, $Z_1$ is a halogen atom or a trifluoromethyl group, $Z_2$ is hydrogen atom on a halogen atom, and A is a —CH— group or a nitrogen atom, and a benzoyl urea compound (II) having the formula:

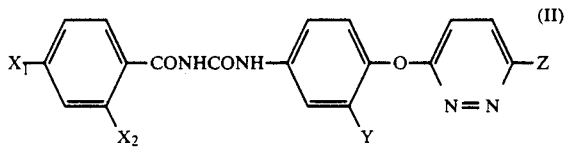

wherein each of $X_1$ and $X_2$ is a hydrogen atom, a halogen atom or a nitro group, provided that when Y is a nitro group, $X_1$ is a hydrogen atom, Y is a hydrogen atom, a halogen atom, a nitro group or a trifluoromethyl group, and Z is a hydrogen atom, a halogen atom or a trifluoromethyl group, as an active ingredient; an effective amount of a nonionic surfactant as a dispersant; and an effective amount of at least one member selected from the group consisting of a cellulose, silicic anhydride, a sucrose fatty acid ester and polyoxyethylene polyoxypropylene glycol, as a distintegrator and wherein the ratio of the benzoyl urea compound (A):the dispersant:the distintegrator is 1 to 70:1 to 30:1 to 90 by weight.

2. The pharmaceutical composition according to claim 1 wherein the nonionic surfactant as a dispersant has at least 3 Hydrophile-Lipophile Balance value.

3. The pharmaceutical composition according to claim 1 wherein the nonionic surfactant as a dispersant is at least one selected from the group consisting of polyoxyethylene hardened castor oil, polyoxyethylene polyoxypropylene glycol, a sucrose fatty acid ester, a glycerol fatty acid ester, a sorbitan fatty acid ester, a propylene glycol fatty acid ester, a polyglycerol fatty acid ester, a polyoxyethylene sorbitan fatty acid ester, a polyoxyethylene sorbitol fatty acid ester, a polyoxyethylene glycerol fatty acid ester, a polyethylene glycol fatty acid ester and a polyoxyethylene castor oil.

4. The pharmaceutical composition according to claim 1 wherein the dispersant is at least one selected from the group consisting of a polyoxyethylene hardened ester oil, a polyoxyethylene polyoxypropylene glycol and a polyglycerol fatty acid ester.

5. The pharmaceutical composition according to claim 1 wherein the disintegrator is at least one selected from the group consisting of a sucrose fatty acid ester and a polyoxyethylene polyoxypropylene glycol.

6. The pharmaceutical composition according to claim 1 wherein the dispersant is at least one selected from the group, consisting of a polyglycerol fatty acid ester and a polyoxyethylene hardened castor oil and the disintegrator is a sucrose fatty acid ester.

7. The pharmaceutical composition according to claim 1 which is in the form of a dry formulation.

8. The pharmaceutical composition according to claim 7, which is prepared by pulverizing the benzoyl urea compound (A) in an aqueous solution containing the dispersant, then adding the disintegrator thereto, followed by freeze-drying.

9. The pharmaceutical composition according to claim 1, wherein the ratio of the benzoyl urea compound (A):the dispersant:the disintegrator is 20 to 50:2 to 20:10 to 70 by weight.

10. The pharmaceutical composition according to claim 1, wherein the dispersant and the disintegrator are different from each other.

* * * * *